US00PP34554P2

(12) United States Plant Patent
Shoup

(10) Patent No.: US PP34,554 P2
(45) Date of Patent: Sep. 13, 2022

(54) HYBRID TEA ROSE PLANT NAMED 'FEMME FATALE'

(50) Latin Name: *Rosa hybrida*
Varietal Denomination: Femme Fatale

(71) Applicant: George Michael Shoup, Brenham, TX (US)

(72) Inventor: George Michael Shoup, Brenham, TX (US)

( * ) Notice: Subject to any disclaimer, the term of this patent is extended or adjusted under 35 U.S.C. 154(b) by 0 days.

(21) Appl. No.: 17/484,931

(22) Filed: Sep. 24, 2021

(51) Int. Cl.
*A01H 5/02* (2018.01)
*A01H 6/74* (2018.01)

(52) U.S. Cl.
USPC ..... Plt./107
CPC ..... *A01H 6/749* (2018.05)

(58) Field of Classification Search
USPC ..... Plt./107
CPC ..... A01H 6/749; A01H 5/02
See application file for complete search history.

*Primary Examiner* — Keith O. Robinson

(57) ABSTRACT

A new and distinct variety of shrub rose plant, herein referred to by its cultivar name, 'Femme Fatale', is provided which abundantly, and continuously forms deep pink colored blooms. The growth habit is upright and sturdy. The foliage is dark green in color with a rough texture. The plant propagates from cuttings easily and uniformly. The blossoms are exceptionally fragrant, and exceptionally heat tolerant. The new variety is well suited to growing in warm climates, and as a source of attractive ornamentation and fragrance in in the landscape.

1 Drawing Sheet

Botanical/commercial classification:
Latin name—*Rosa hybrida.*
Varietal denomination: 'Femme Fatale'.

SUMMARY OF THE INVENTION

The new variety of *Rosa hybrida* Hybrid Tea rose plant was created at Brenham, Tex., U.S.A., by artificial pollination wherein two parents were crossed which previously had been observed in the hope that each would contribute their desired traits. The female parent (i.e., the seed parent) was a non-patented seedling variety named 'Komodo'. 'Komodo' is derived from the varieties 'Proud Land' (U.S. Plant Pat. No. 2,737) and 'Radbrite' (U.S. Plant Pat. No. 17,391). The male parent (i.e., the pollen parent) was the 'TEXpeaswi' variety (non-patented). The parentage of the new variety can be summarized as follows:

'Komodo' x 'TEXpeaswi'

The seeds resulting from the above pollination were stratified in an artificial environment and sown into trays in a greenhouse environment. Seedlings were obtained and displayed phenotypic and biological variation. Selective trialing and evaluation of the seedlings resulted in the identification of a single plant of the new variety.

It was found that the new Hybrid Tea rose plant of the present invention possesses the following combination of characteristics:

(a) abundantly, and continuously forms deep pink colored blooms,
(b) exhibits an upright and sturdy growth habit,
(c) exhibits exceptionally fragrant blooms,
(d) forms disease resistant foliage that is dark green in color and rough in texture,
(e) exhibits exceptional heat tolerance, and (f) is well suited for growing in warm climates, and as a source of attractive ornamentation and fragrance in in the landscape.

The new rose can be readily distinguished from its ancestors upon inspecting the blossoms. More specifically, the 'Femme Fatale' variety forms blossoms which are deep pink in coloration, while the parental variety 'TEXpeaswi' forms dissimilar blossoms which are striped, apricot and pink in color. The new variety can also be readily distinguished from its ancestors upon observing the fragrance of the blossoms. 'Femme Fatale' produces blossoms with an exceptionally strong damask fragrance, while the parental varieties 'Komodo' and 'TEXpeaswi' produce blossoms which are mild in fragrance.

The new variety of the present invention also can be readily distinguished from other hybrid tea rose plants, including the 'Miss All-American Beauty' variety (U.S. Plant Pat. No. 2,625) upon observation of the disease resistance of the foliage. For example, the 'Miss All-American Beauty' variety forms foliage which is susceptible to black spot *Diplocarpon rosae*, which is dissimilar to the foliage of 'Femme Fatale' which is resistant to black spot *Diplocarpon rosae.*

Asexual reproduction of 'Femme Fatale' was done by taking cuttings in Brenham Tex., U.S.A. in beginning in 2019. Cuttings were taken from mature stems that were approximately 10 to 15 cm in length and approximately 0.75 cm in diameter. Initial cuttings were taken of the new variety and grew into mature plants. Subsequent cuttings were taken of the initial asexually reproduced plants and grown into mature plants. Mature plants of both the initially propagated plants and the subsequently propagated plants were compared. There was no observable difference between the generations. Therefore, it was demonstrated that the characteristics of 'Femme Fatale' remain stable, uniform, and true to type in successive generations of asexual reproduction.

BRIEF DESCRIPTION OF THE DRAWING

The accompanying color illustration shows as true is as is reasonably possible to obtain in color photographs of this type, the typical characteristics of the plant parts, i.e., the flowers, buds, stems and leaves of the new rose, 'Femme Fatale'. The illustrated rose plant parts were approximately one year of age and were observed during August, while growing on their own roots in Brenham, Tex., U.S.A. Flowers, buds, and stem growth are displayed in various stages of maturity. The upper side and under side of the leaves, blooms and petals are displayed.

DETAILED BOTANICAL DESCRIPTION

The chart used in the identification of colors is The Royal Horticultural Society Colour Chart (R.H.S. Colour Chart) Edition V (2007). The description is based one year old specimens of the new variety during August while growing outdoors on their own roots at Brenham, Tex., U.S.A.

Class: Hybrid Tea Rose. Cultivar 'Femme Fatale'.

Plant:

*Height*.—Approximately 0.75 m on average at maturity.

*Width*.—Approximately 0.6 m on average at maturity.

*Habit*.—Erect.

Stems:

*Size*.—Approximately 72 cm tall by 1.2 cm in caliper.

*Color*.—Immature: Turquoise-Green Group 144A. Mature: Turquoise-Green Group 141A.

*Prickles*.—Size: Approximately 0.9 cm in length on average. Quantity: Approximately 20 prickles present per every 15 cm of stems. Color: Turquoise-Green Group 144A. Shape: Declining Density: Average.

*Texture*.—Smooth.

*Internodal spacing*.—Approximately 3 cm on average.

Leaves:

*Arrangement*.—Alternate, odd-pinnate, and compound.

*Margin*.—Serrate.

*Stipules*.—Size: Approximately 3 cm×0.4 cm on average. Margin: Adnate, and gland-ciliate edges. Color: Turquoise-Green Group 141A. Texture: Smooth.

*Size*.—Approximately 12.5 cm×7.75 cm on average.

*Petioles*.—Color upper surface: Turquoise-Green Group 140A. Color under surface: Turquoise-Green Group 152B. Size: Approximately 6.25 cm in length on average and approximately 1 mm in width on average. Shape: Filiform.

*Glossiness of the upper side of the leaf*.—Medium.

*Leaflets*.—Number: 5 and 7. Shape: Oblong. Size: Approximately 5 cm×3.5 cm on average. Venation: Reticulate. Venation Color: Turquoise-Green Group 140A. Apex: Obtuse. Base: Obtuse. Undulation of Margin: Very weak. Texture Upper Surface: Slightly rugose. Texture Under Surface: Matte. Overall Appearance: Dark green, rough. Color (Young Foliage) Upper Surface: Turquoise-Green Group 152A. Color (Young Foliage) Under Surface: Yellow-Red Group N34A. Color (Adult Foliage) Upper Surface: Turquoise-Green Group 141A. Color (Adult Foliage) Under Surface: Turquoise-Green Group 143A.

Inflorescence:

*Number of flowers per inflorescence*.—Approximately 1 to 3 on average.

*Florescence type*.—Solitary to paniculate.

*Peduncle*.—Color: Turquoise-Green Group 144A. Length: Approximately 4 cm on average. Diameter: Approximately 3 mm on average. Texture: Slightly gland-ciliate.

*Sepals*.—Number: 5. Arrangement: Pentamerous and imbricate. Shape: Ovate-acuminate. Margin: Pinnatifid to lacerate. Sepal Extensions: Medium. Apex: Lanceolate. Base: Truncate. Texture: Slightly glandular. Color Upper Surface: Turquoise-Green Group 144A. Color Under Surface: Turquoise-Green Group 144A.

*Buds*.—Shape: Conical. Size: Approximately 2 cm in length to 1.5 cm in width on average. Color (When Opening) Inner Surface: Yellow-Red Group 44A towards the base, and Yellow-Red Group 46B towards the apex. Color (When Opening) Outer Surface: Yellow-Red Group 45A to 45B.

Flower:

*Form*.—Hybrid tea, double.

*Shape*.—Round.

*Profile of the lower part of the flower*.—Convex.

*Diameter*.—Approximately 8 cm on average.

*Color*.—(When Opening) Upper Surface: Yellow-Red Group 44A towards the base, and Yellow-Red Group 46B towards the apex. (When Opening) Under Surface: Yellow-Red Group 45A to 45B. (When Blooming) Upper Surface: Yellow-Red Group 44A towards the base, and Yellow-Red Group 46B towards the apex. (When Blooming) Under Surface: Yellow-Red Group 45A to 45B. (End Of Blooming) Upper Surface: Yellow-Red Group 51A. (End Of Blooming) Under Surface: Yellow-Red Group 54A.

*Fragrance*.—Damask and citrus.

*Petal form*.—Suborbicular.

*Petals*.—Size: Approximately 3.4 cm×3.4 cm on average. Margins: Entire. Shape: Obcordate. Apex: Rounded. Base: Acute. Texture: Smooth. Basal Spot: Absent. Number: Approximately 27 on average, none of which are petaloids. Petal Drop: Petals remain on the plant for approximately 3 days after the end of blooming.

*Stamen number*.—Approximately 165 on average.

*Anther color*.—Yellow-Red Group 28B.

*Anther shape*.—Oblong with chordate base.

*Anther length*.—Approximately 2 mm on average.

*Filament color*.—Yellow-Red Group 40A.

*Filament length*.—Approximately 0.75 cm on average.

*Pollen quantity*.—Average amount of pollen produced.

*Pollen color*.—Yellow-Red Group 25A.

*Pistil form*.—Free and exerted.

*Pistil number*.—Approximately 90 on average.

*Stigma color*.—Brown-Grey Group 197A.

*Style color*.—Yellow-Red Group 53A.

*Style length*.—Approximately 2 mm on average.

*Receptacle*.—Globose. Achenes form on the inside of the fruit.

*Rate of flower opening*.—Average rate of flower opening.

*Lasting quality*.—On plant: Approximately 3 to 4 days on average. In vase: Unknown.

Development:

*Vegetation*.—Dense.

*Growth rate*.—Average rate of growth.

*Hip/seed formation*.—Occasional hip formation.

Root system:

*Root color*.—Yellow-Red Group 19D.

*Root habit*.—Well rounded.

Physiology:

*Disease resistance*.—Above average resistance to black spot *Diplocarpon rosae*, and powdery mildew *Podosphaera pannosa*.

*Cold hardiness*.—The variety has been found to be suitable for climactic conditions in USDA Plant Hardiness Zone 8. Based on the performance of its parent varieties, it is likely, although untested, that the new variety is also suitable for climatic conditions of USDA Plant Hardiness Zones 6 and 7.

*Heat tolerance*.—The new variety exhibits above average heat tolerance, as blooms do not reduce in size, when temperatures are in excess of 100° F., as compared to parental variety 'TEXpeaswi' which does reduce in size under the aforementioned conditions. The variety has been found to be suitable for climactic conditions in USDA Plant Hardiness Zone 8. Based on the performance of its ancestors, it is likely, although untested, that the new variety is also suitable for climatic conditions of USDA Plant Hardiness Zone 9.

*Drought tolerance*.—The new variety exhibits above average drought tolerance as immature stems do not experience a reduction in turgor pressure when temperatures are in excess of 100° F. This is in comparison to the parental variety 'TEXpeaswi' which does experience a reduction in turgor pressure under the aforementioned conditions.

I claim:

1. A new and distinct variety of shrub rose plant named 'Femme Fatale' characterized by the following combination of characteristics:

(a) abundantly, and continuously forms deep pink colored blooms, (b) exhibits an upright and sturdy growth habit, (c) exhibits exceptionally fragrant blooms, (d) forms disease resistant foliage that is dark green in color and rough in texture, (e) exhibits exceptional heat tolerance, and (f) is well suited for growing in warm climates, and as a source of attractive ornamentation and fragrance in in the landscape.

substantially as illustrated and described herein.

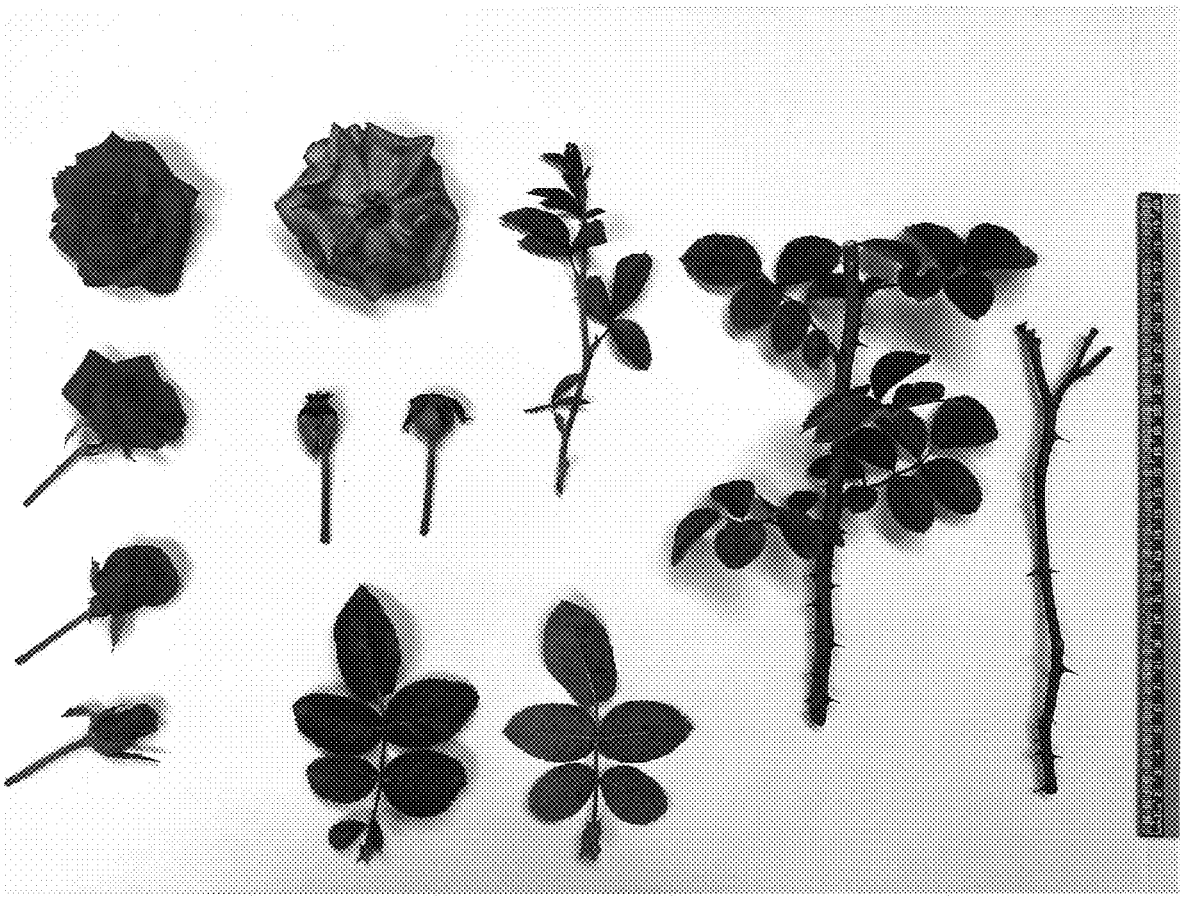

* * * * *